United States Patent
Weng et al.

(10) Patent No.: US 12,383,389 B2
(45) Date of Patent: Aug. 12, 2025

(54) MICROFLUIDIC SYSTEMS AND METHODS TO DENUDE MAMMALIAN OOCYTES

(71) Applicant: The General Hospital Corporation, Boston, MA (US)

(72) Inventors: Lindong Weng, Arlington, MA (US); Gloria Y. Lee, Norwood, MA (US); Mehmet Toner, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 1007 days.

(21) Appl. No.: 17/044,980

(22) PCT Filed: Apr. 4, 2019

(86) PCT No.: PCT/US2019/025895
§ 371 (c)(1),
(2) Date: Oct. 2, 2020

(87) PCT Pub. No.: WO2019/195620
PCT Pub. Date: Oct. 10, 2019

(65) Prior Publication Data
US 2021/0161635 A1 Jun. 3, 2021

Related U.S. Application Data

(60) Provisional application No. 62/732,884, filed on Sep. 18, 2018, provisional application No. 62/652,648, filed on Apr. 4, 2018.

(51) Int. Cl.
*A61D 19/02* (2006.01)
*A61D 19/04* (2006.01)
*C12M 3/06* (2006.01)

(52) U.S. Cl.
CPC ........... *A61D 19/027* (2013.01); *A61D 19/04* (2013.01); *C12M 23/16* (2013.01)

(58) Field of Classification Search
CPC ...... A61D 19/027; A61D 19/04; A61D 19/00; A61D 19/02; C12M 23/16; C12M 21/06;
(Continued)

(56) References Cited

U.S. PATENT DOCUMENTS

| 4,802,591 A | 2/1989 | Lower et al. |
| 7,390,648 B1 | 6/2008 | Palacios-Boyce |

(Continued)

FOREIGN PATENT DOCUMENTS

| CN | 107110765 | 8/2017 |
| WO | WO 2001/088087 | 11/2001 |

(Continued)

OTHER PUBLICATIONS

Office Action in Japanese Appln. No. 2020-554520, dated Jul. 25, 2023, 8 pages (with English translation).

(Continued)

*Primary Examiner* — Sunita Reddy
(74) *Attorney, Agent, or Firm* — Fish & Richardson P.C.

(57) ABSTRACT

Microfluidic systems are configured to process liquid samples that include cumulus-oocyte complexes (COCs), such as raw follicular fluid, in an automated and continuous manner to produce oocytes separate or "denuded" from surrounding cumulus cells. The systems include a substrate and a channel that can have two or more sub-channels. Each channel includes an inlet, an outlet, and one or more stages arranged in series. Each of the stages includes one or more expansion units and one or more constriction units. At least one stage includes constriction units having jagged internal surfaces, e.g., teeth, that help remove the cumulus cells from the COCs.

17 Claims, 10 Drawing Sheets

(58) Field of Classification Search
CPC ....... C12M 3/00; B01L 3/502746; B01L 3/00; A61B 17/00
USPC ...................................................... 600/33–35
See application file for complete search history.

(56) References Cited

U.S. PATENT DOCUMENTS

| | | | |
|---|---|---|---|
| 2006/0118479 A1* | 6/2006 | Shevkoplyas | G01N 33/491 209/208 |
| 2006/0128006 A1* | 6/2006 | Gerhardt | C12M 47/04 438/1 |
| 2007/0059680 A1* | 3/2007 | Kapur | B01L 3/502753 435/6.12 |
| 2007/0059719 A1* | 3/2007 | Grisham | B01L 3/502753 705/2 |
| 2009/0029471 A1* | 1/2009 | Palacios-Boyce | C12M 35/04 438/106 |
| 2011/0084033 A1* | 4/2011 | Rodriguez Villarreal | B01D 21/0087 210/252 |
| 2012/0322097 A1* | 12/2012 | Charest | C12M 41/00 435/286.1 |
| 2014/0287509 A1* | 9/2014 | Sharei | C12M 1/02 435/375 |
| 2014/0377866 A1* | 12/2014 | Haun | B01L 3/502753 435/379 |
| 2015/0031012 A1 | 1/2015 | Palermo | |
| 2015/0184127 A1 | 7/2015 | White et al. | |
| 2016/0123858 A1* | 5/2016 | Kapur | B01L 3/502753 73/61.71 |
| 2017/0166865 A1* | 6/2017 | Peng | A61B 17/435 |
| 2018/0282676 A1* | 10/2018 | Vollmer | C12M 21/06 |
| 2019/0275520 A1* | 9/2019 | Stewart | C12M 35/04 |

FOREIGN PATENT DOCUMENTS

| | | | |
|---|---|---|---|
| WO | WO-2006097740 A1 * | 9/2006 | ............ B01L 3/5027 |
| WO | WO 2017/055361 | 4/2017 | |
| WO | WO 2017/173373 | 10/2017 | |

OTHER PUBLICATIONS

EA Office Action in Eurasian Appln. No. 202092390, dated Apr. 30, 2021, 5 pages (with English translation).

EP Extended European Search Report in European Appln. No. 19780966.8, dated May 31, 2021, 8 pages.

PCT International Preliminary Report on Patentability in International Appln. No. PCT/US2019/025895, dated Oct. 15, 2020, 10 pages.

PCT International Search Report and Written Opinion in International Appln. No. PCT/US2019/025895, dated Jul. 5, 2019, 12 pages.

Weng et al., "On-chip oocyte denudation from cumulus-oocyte complexes for assisted reproductive therapy," Lab Chip, 2018, 18(24):3892-3902.

Office Action in Indian Appln. No. 202047046662, dated Dec. 9, 2022, 6 pages.

Office Action in Australian Appln. No. 2019247412, dated Oct. 13, 2022, 3 pages.

Office Action in Chinese Appln. No. 201980033958.1, dated Oct. 21, 2022, 23 pages (with English translation).

Notice of Acceptance in Australian Appln. No. 2019247412, dated Jun. 21, 2023, 3 pages.

Office Action in Japanese Appln. No. 2020-554520, dated Feb. 7, 2023, 12 pages (with English translation).

Office Action in Canadian Appln. No. 3,096,048, dated Oct. 31, 2023, 4 pages.

Office Action in Israeli Appln. No. 277771, dated Aug. 31, 2023, 7 pages.

Office Action in Japanese Appln. No. 2020-554520, dated Dec. 12, 2023, 5 pages (with English translation).

Notice of Allowance in Japanese Appln. No. 2020-554520, dated Jul. 16, 2024, 6 pages (with English translation).

* cited by examiner

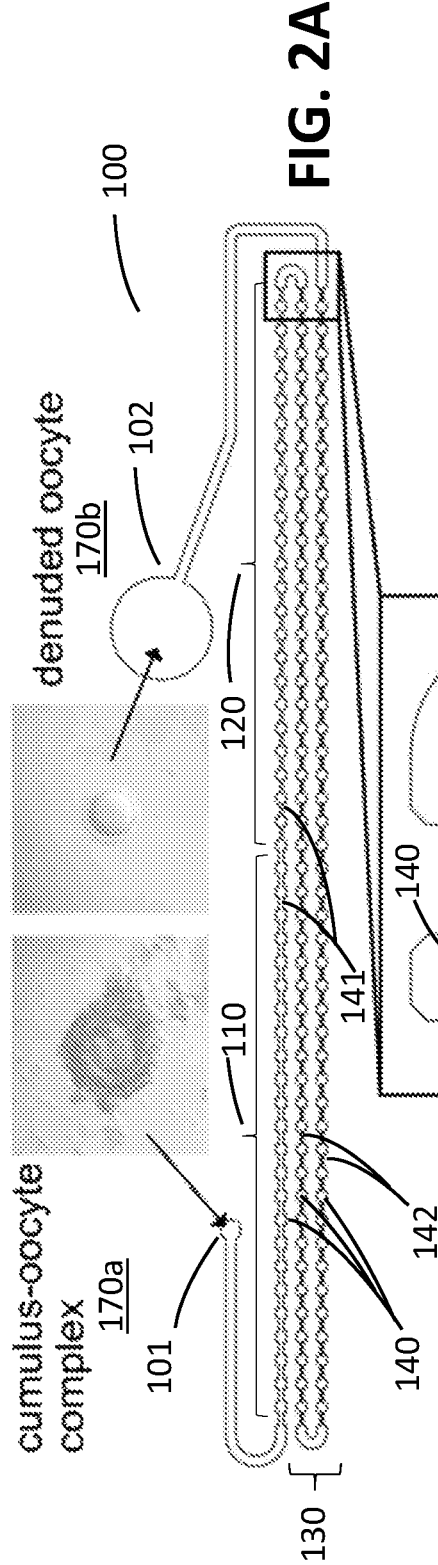
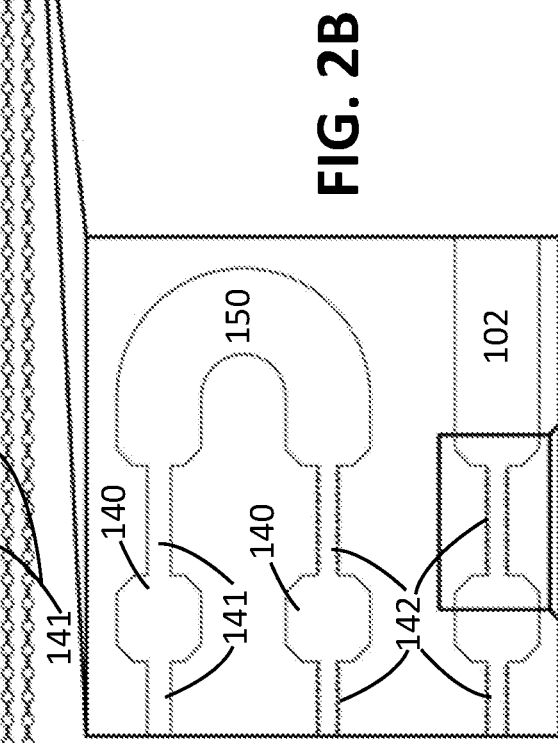
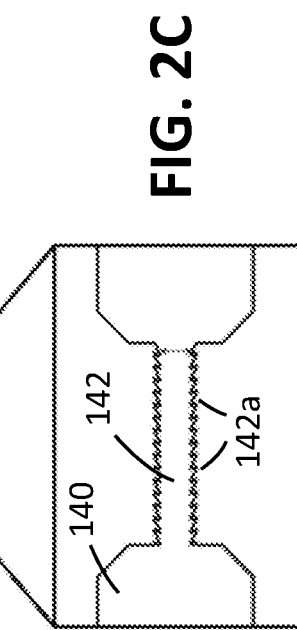
FIG. 2A
FIG. 2B
FIG. 2C

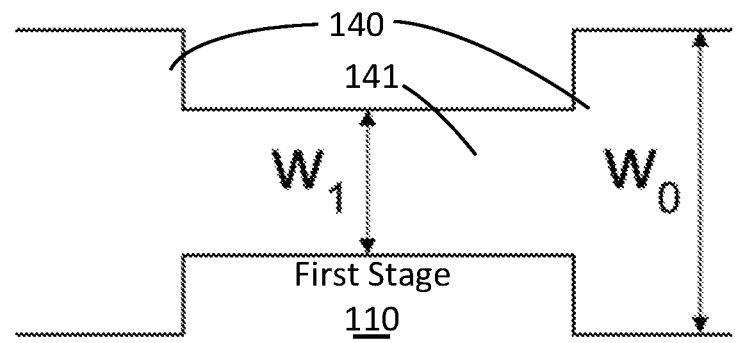
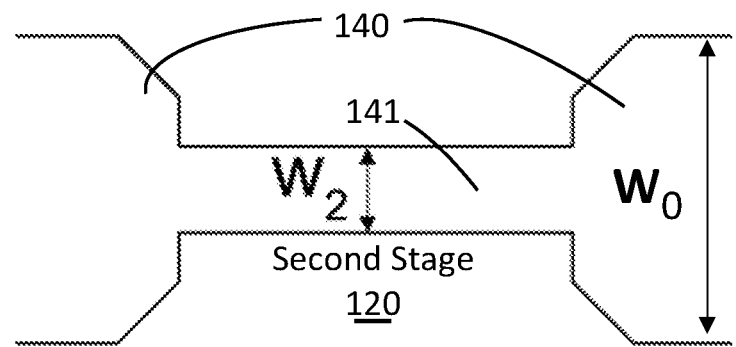
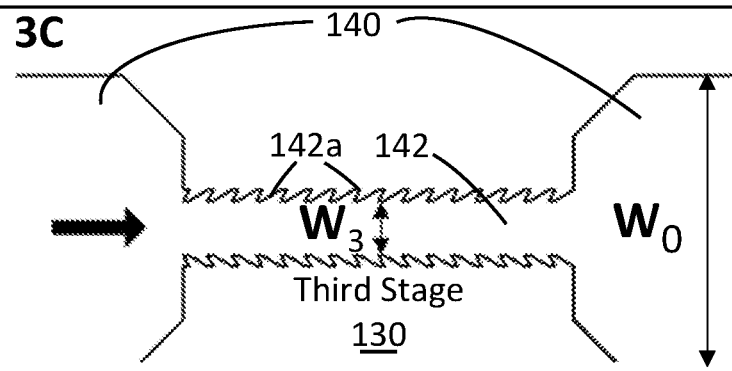

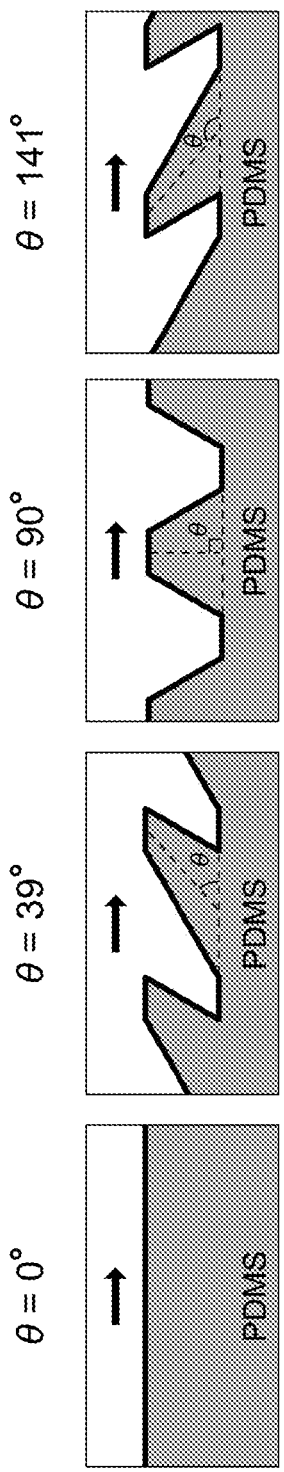
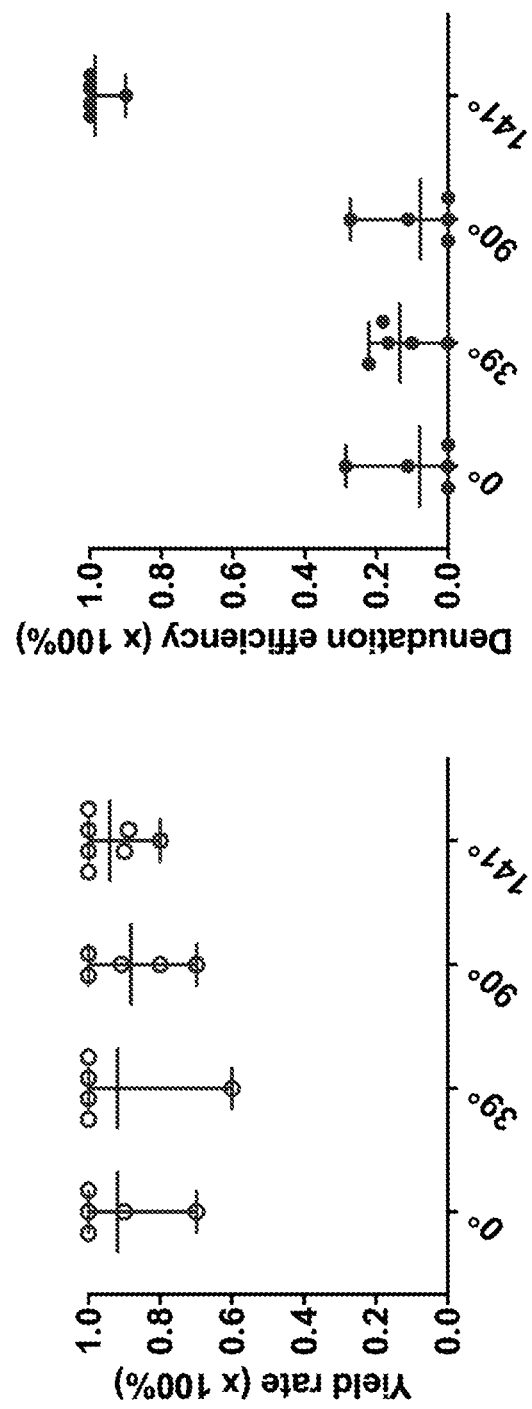
FIG.8A
FIG.8B
FIG.8C

| Flow Rate | # of Oocytes (Inlet) | # of Oocytes (Outlet) | # of Clean Oocytes | Yield Rate | Denudation Efficiency |
|---|---|---|---|---|---|
| 5 mL/min | 10 | 9 | 8 | 90% | 89% |
| 5 mL/min | 10 | 8 | 4 | 80% | 50% |
| 3 mL/min | 10 | 9 | 5 | 90% | 56% |
| 4 mL/min | 10 | 10 | 6 | 100% | 60% |
| 5 mL/min | 10 | 10 | 9 | 100% | 90% |
| 5 mL/min | 31 | 31 | 30 | 100% | 97% |
| 5 mL/min | 16 | 16 | 14 | 100% | 88% |
| 5 mL/min | 13 | 13 | 12 | 100% | 92% |
| 5 mL/min | 15 | 15 | 15 | 100% | 100% |

FIG. 10

MICROFLUIDIC SYSTEMS AND METHODS TO DENUDE MAMMALIAN OOCYTES

CROSS-REFERENCE TO RELATED APPLICATION

This application is a 371 U.S. National Stage Entry of PCT/US2019/025895, filed on Apr. 4, 2019, which claims the benefit of U.S. Provisional Patent Application Ser. No. 62/732,884, filed on Sep. 18, 2018, and U.S. Provisional Patent Application Ser. No. 62/652,648, filed on Apr. 4, 2018. The entire contents of the prior applications are hereby incorporated by reference.

BACKGROUND

Assisted reproductive technology (ART), such as In Vitro fertilization (IVF), can be used to treat infertility or genetic problems and assist with the conception of a child. During IVF, mature eggs (oocytes) can be retrieved from the ovaries and fertilized by sperm in a lab. Then the fertilized egg, known as the embryo, can be implanted in the uterus. IVF involves several steps: ovulation induction, oocyte retrieval, sperm retrieval, fertilization, and embryo transfer. In conventional IVF, eggs are placed in a lab dish in culture media together with prepared sperm where the eggs and sperm are allowed to fertilize spontaneously overnight.

Intracytoplasmic sperm injection (ICSI) can differ from traditional IVF in that each egg can be individually injected with a single sperm using a tiny needle under microscopic guidance. ICSI has been recognized as the only treatment for male factor infertility. For effective ICSI procedures, the denudation of oocytes before microinjection can be important, as the oocytes can be surrounded by several layers of specialized granulosa cells (cumulus cells), forming the cumulus-oocyte complex (COC). In typical clinic operations, oocytes can be denuded using a combination of enzymatic (hyaluronidase) and mechanical (manual pipetting) methods, which may have to be performed by well-trained personnel.

SUMMARY

This disclosure provides microfluidic systems for denuding oocytes from surrounding cumulus and corona cells with broad applications in the field of assisted human reproduction. The systems include one or more channels having repeating constriction units and expansion units. In general, samples containing COCs, either a collection of only COCs in a buffer or other liquid, or raw follicular fluid from patient that contains COCs, blood clots, and tissue debris of varying sizes, are injected into an inlet port of the system and as the sample flows through the system's channel or channels, the constriction units and the expansion units work together to facilitate the denudation of the oocytes. For example, the constriction units can include surface features, such as jagged or smooth inner surfaces, for applying mechanical stress to the COCs. In some implementations, the expansion units promote tumbling of the COCs as they make their way through the system. In some embodiments, the systems are configured in such a manner that a continuous flow of COCs is achieved.

In one aspect, the present disclosure provides systems for denuding oocytes from attached cumulus cells. The systems include a substrate and a channel or two or more sub-channels. Each channel includes an inlet, an outlet, and one or more stages arranged in series within the channel. Each stage of the one or more stages is in fluid communication with a subsequent stage. Each of the one or more stages includes one or more expansion units and one or more constriction units. At least one stage of the one or more stages includes one or more constriction units having two opposing walls. One or each of the opposing walls includes a jagged surface facing the inside of the channel. The jagged internal surface includes a plurality of teeth arranged such that the plurality of teeth on a first opposing wall are pointed towards the plurality of teeth on a second opposing wall. The tips of the plurality of teeth on the first opposing wall are an equal distance from tips of the plurality of teeth on the second opposing wall, e.g., the teeth are arranged in parallel.

In another aspect, the disclosure provides systems for denuding oocytes from attached cumulus cells that include a substrate; and a channel having an inlet, an outlet, and one or more stages arranged in series between the inlet and the outlet, wherein each stage is in fluid communication with a subsequent stage, wherein each stage includes one or more expansion units and one or more constriction units, and wherein at least one of the stages includes one or more constriction units each having two opposing walls, wherein at least one of the two opposing walls comprises a jagged internal surface comprising a plurality of teeth.

In some embodiments, each of the two opposing walls in each constriction unit includes a plurality of teeth and wherein the plurality of teeth on a first opposing wall are pointed towards the plurality of teeth on a second opposing wall. For example, tips of the plurality of teeth on the first opposing wall and tips of the plurality of teeth on the second opposing wall can be arranged in parallel, and a distance between the tips of teeth on the first and second opposing walls can be about the diameter of an oocyte to be denuded.

In some embodiments, at least one of the stages includes one or more expansion units alternating with one or more constriction units.

In some embodiments, one or more of the plurality of teeth, e.g., all of the teeth, are set at an angle from about 30 degrees to about 90 degrees against a direction of flow through the channel.

In various embodiments, at least one stage of the one or more stages includes one or more constriction units having a smooth internal surface. In some embodiments, at least one expansion unit has a width of about 250 to about 600 microns and/or at least one constriction unit has a width of about 100 to about 350 microns.

In another aspect, the disclosure provides systems for denuding oocytes from attached cumulus cells, that include a substrate and a channel that includes an inlet, an outlet, and three stages arranged in series with each stage in fluid communication with the next stage, wherein the first stage comprises a series of first expansion units alternating with first constriction units, wherein the first expansion units have a first width and the first constriction units have a second width, and a smooth internal surface; wherein the second stage comprises a series of second expansion units alternating with second constriction units, wherein the second expansion units have a third width and the second constriction units have a fourth width, and a smooth internal surface; and wherein the third stage comprises a series of third expansion units alternating with third constriction units, wherein the third expansion units have a fifth width and the third constriction units have a sixth width and at least two opposing walls, wherein the two opposing walls each comprises a jagged internal surface comprising a plurality of teeth arranged such that the plurality of teeth on a first opposing wall of the third constriction units are pointed towards the plurality of teeth on a second opposing wall of the third constriction units and wherein tips of the plurality of teeth on the first opposing wall and tips of the plurality of teeth on the second opposing wall are arranged in parallel.

In certain embodiments of the systems described herein, the channel has a height of about 200 to 300 microns. In some embodiments, the teeth are set at an angle from about 30 degrees to about 90 degrees against a direction of flow through the channel.

In certain embodiments, the first width can be about 250 to about 600 microns, e.g., 250, 275, 300, 325, 350, 375, 400, 425, 450, 475, 500 525, 550, 575, or 600 microns. The first width can be about 500 microns. The second width can about 200 to about 350 microns, e.g., 200, 225, 250, 275, 300, 325, or 350 microns. The second width can be about 230 to 260 microns, e.g., 235, 240, 245, 250, 255, or 260 microns. The third width can be about 250 to about 600 microns with possible dimensions as noted above. The third width can be about 500 microns, e.g., 400, 425, 450, 475, 500, 525, 550, or 600 microns. The fourth width can be about 100 to about 250 microns, e.g., 100, 125, 150, 175, 200, 225, or 250 microns. The fourth width can be about 130 to about 160 microns, e.g., 130, 135, 140, 145, 150, 155, or 160 microns. The fifth width can be about 250 to about 600 microns with possible dimensions as noted above. The fifth width can be about 500 microns, e.g., 400, 425, 450, 475, 500, 525, 550, or 600 microns. The sixth width can about 70 to about 120 microns, e.g., 70, 75, 80, 85, 90, 95, 100, 105, 110, 115, or 120 microns. The sixth width can be about 90 to about 120 microns, e.g., 95, 100, 105, 110, 115, or 120 microns.

In certain embodiments, the first width is about 500 microns, the second width is about 230 to 260 microns, the third width is about 500 microns, the fourth width is about 130 to about 160 microns, the fifth width is about 500 microns, the sixth width is about 90 to about 120 microns, and the distance between the tips of the teeth is about 90 to about 110 microns.

In another aspect, this disclosure provides systems for denuding oocytes from attached cumulus cells in a liquid sample, that include a substrate; and a channel having an inlet, an outlet, and one or more stages arranged in series between the inlet and the outlet, wherein each stage is in fluid communication with a subsequent stage, wherein each stage comprises one or more rows of a plurality of posts arranged across the channel, wherein posts in a given row are spaced apart from neighboring posts within the row to define a sub-channel between each neighboring pair of posts, and wherein each of a plurality of posts in at least one stage includes a pair of walls arranged to face either an opposing wall of a neighboring post within a same row or to face an inner wall of the channel, and wherein at least one of the walls on each of the plurality of posts comprises a jagged internal surface comprising a plurality of teeth.

In some embodiments, opposing walls of neighboring posts in a row each include a plurality of teeth arranged to point towards each other. In various embodiments, at least one sub-channel of a first stage has a width of about 240 to 260 microns, and the first stage includes rows of posts arranged to filter debris from the fluid sample. In some embodiments, at least one sub-channel of a second stage has a width of about 140 to 160 microns, and the second stage includes rows of posts arranged to filter debris from the fluid sample. In certain embodiments, at least one sub-channel in a third stage has a width of about 90 to 110 microns, the third stage includes rows of posts arranged to denude oocytes, and one or more posts in each row includes a plurality of jagged teeth.

In some embodiments, all of the posts in the third stage include a pair of walls arranged to face either an opposing wall of a neighboring post within a same row or to face an inner wall of the channel, and each of the walls on each of the posts in the third stage includes a jagged internal surface comprising a plurality of teeth.

In certain embodiments, all of the sub-channels of a first stage have a first width and all of the sub-channels of a second stage have a second width less than the first width. In some embodiments, all of the sub-channels of a third stage have a third width being less than the second width.

In another aspect, the disclosure provides methods of removing cumulus cells from oocytes in a liquid sample. The methods include obtaining a liquid sample including one or more oocytes; injecting the liquid sample into the inlet of any of the systems described herein; flowing the liquid sample through the one or more stages of the channel at a flow rate; and retrieving oocytes from the outlet.

In certain embodiments of these methods, the liquid sample can be or include a follicular fluid, a culture medium, or a buffer medium.

In some embodiments, the flow rate is approximately constant and is about 0.5 to about 5.0 ml/minute, e.g., about 1.0 ml/minute to about 4.0 ml/minute, e.g., the flow rate can be about 0.5 to about 2.0 ml/minute, e.g., 0.5, 0.6, 0.7, 0.8, 0.9, 1.0, 1.1, 1.2, 1.3, 1.4, 1.5, 1.6, 1.7, 1.8, 1.9, or 2.0 ml/minute. The flow rate can be about 1.0 ml/minute. The oocytes can be mammalian oocytes, e.g., human oocytes. The width of the contracting units of the third stage can be about 100 to 110 microns, e.g., 100, 102, 104, 106, 108, or 110 microns. In some embodiments, the oocytes are human oocytes and a distance between tips of the plurality of teeth on opposing walls is about 100 to 110 microns.

In various embodiments, at least one of the one or more stages includes one or more expansion units alternating with one or more constriction units. At least one stage of the one or more stages can include one or more constriction units having a smooth internal surface. At least one expansion unit can have a width of about 250 to about 600 microns, e.g., 250, 275, 300, 325, 350, 375, 400, 425, 450, 475, 500 525, 550, 575, or 600 microns. At least one constriction unit can have a width of about 200 to about 350 microns, e.g., 200, 225, 250, 275, 300, 325, or 350 microns. At least one constriction unit can have a width of about 100 to 250 microns, e.g., 125, 150, 175, 200, 225, or 250 microns, or more.

In another aspect, the present disclosure provides systems having a channel including multiple sub-channels for denuding oocytes from attached cumulus cells. The systems include a substrate and a channel. The channel includes an inlet, an outlet, and one or more stages arranged in series within the channel. Each stage of the one or more stages is in fluid communication with a subsequent stage. Each of the one or more stages includes one or more posts aligned in a row that is arranged across the channel, e.g., perpendicular to the channel. The posts can be ovals, squares, rectangles, or the like, as long as they have two elongate, e.g., straight, walls, e.g., that run in parallel to each other. Each of the rows includes a plurality of posts, e.g., two or more, e.g., 2, 3, 4, 5, 6, 7, 8, 9, 10, or more posts. Each of the posts of a given row is spaced apart from a neighboring post within the given row to define a sub-channel. One or more of the posts in a row includes a plurality of jagged teeth or other surface roughness on the elongate, straight walls of the posts facing a wall of the channel or facing another post in the row.

At least one sub-channel can have a width of about 240 microns, e.g., 200, 210, 220, 230, 240, 250, 260, 270, or 280 microns. At least one sub-channel can have a width of 140 microns, e.g., 120, 130, 140, 150, or 160 microns. At least one sub-channel can have a width of about 90 microns, e.g., 80, 85, 90, 95, 100, or 105 microns.

All of the posts can include a plurality of jagged teeth, e.g., along a strait wall of the post. All of the sub-channels of the first stage can have a first width and all of the sub-channels of the second stage can have a second width being less than the first width. All of the sub-channels of the third stage can include a third width being less than the second width.

The present disclosure relates to systems and methods that seek to solve disadvantages in the field of ART. At least one advantage of the systems described herein is that they provide a means for denuding oocytes using a continuous fluid flow. Another advantage of the present systems is that they enable simpler, automated methods for denuding oocytes. In addition, the new systems can handle raw follicular fluid or liquid samples that include significant debris in the form of blood cells, blood clots, portions of tissues, etc., while still providing an excellent yield of denuded oocytes. Moreover, compared with other devices, systems, and conventional manual procedures for denuding oocytes, the present systems and methods decrease the probability that the fertilization or developmental potential of the oocyte becomes compromised. Therefore, the new systems and methods provide an efficient and effective method for processing human oocytes in an automated, standardized, and continuous manner.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 2A-2C are schematic illustrations of a microfluidic system with one channel for removing cumulus cells from cumulus-oocyte complexes (COCs), according to the present disclosure.

FIG. 3A is a schematic diagram that shows an enlargement of a smooth constriction unit and proximate expansion units located in a first stage of a channel within a microfluidic system according to an embodiment of the present disclosure.

FIG. 3B is a schematic diagram that shows an enlargement of a smooth constriction unit and proximate expansion units located in a second stage of a channel within a microfluidic system according to an embodiment of the present disclosure.

FIG. 3C is a schematic diagram that shows an enlargement of a jagged constriction unit and proximate expansion units located in a third stage of a channel within a microfluidic system according to an embodiment of the present disclosure.

FIG. 8A is an illustration of four different implementations ($\theta=0°$, $39°$, $90°$ and $141°$) of jagged teeth tilting along a constriction unit in a channel.

FIGS. 8B and 8C are graphs that show the yield rate and denudation efficiency of the microfluidic system featuring different tilting angles $\theta$. Denudation efficiency is highest for a tilting angle of $141°$ tilting against the direction of flow shown by the arrow.

FIG. 10 is a chart that shows the effect of flow rate on the yield rate and denudation efficiency of the microfluidic system having multiple sub-channels.

DETAILED DESCRIPTION

Figure 1:
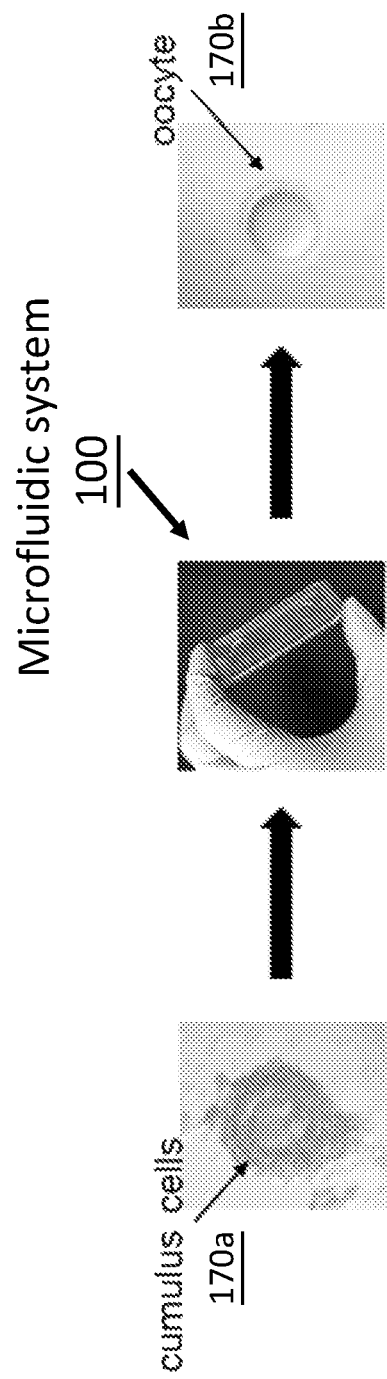
FIG. 1 is a schematic illustrative overview of the methods for using a microfluidic system, according to at least one exemplary embodiment of the present disclosure.

Assisted reproductive technologies (ART), such as in vitro fertilization (IVF) and intracytoplasmic sperm injection (ICSI), are increasingly popular methods to treat infertility. However, typical ART procedures can suffer from a variety of limitations, such as being costly and time consuming. Typical ART procedures also rely on highly skilled technicians, such as embryologists, which can result in variation from operator to operator and a lack of standardization. For ICSI to be effective, it is typically important to denude the oocytes before the procedure to facilitate the injection of sperm into the oocyte and to allow for the evaluation of oocyte morphology, in particular, the nuclear maturation stage.

In clinical ICSI practice, embryologists first need to handpick about a dozen of cumulus-oocyte complexes (COCs) from approximately 150 mL follicular fluid under a microscope. Oocytes originally retrieved from the ovaries are typically surrounded by several layers of specialized granulosa cells (cumulus cells), forming an organized structure known as the cumulus-oocyte complex (COC). Follicular fluid samples are typically 20 to 200 mL in volume and contain some debris, some tissue pieces, coagulated blood cells, blood cells, and COCs. Then, embryologists need to denude oocytes using a combination of enzymatic (e.g., hyaluronidase) and mechanical (manual pipetting) methods before intracytoplasmic sperm injection.

The cumulus cells that are in close contact with the oocyte, also known as corona cells, can develop cytoplasmic projections that cross the zona pellucida and form gap junctions with the oolemma. In typical procedures, oocytes can be denuded from the cumulus-corona cell mass via enzymatic action of hyaluronidase and manual pipetting. However these types of procedures can be inefficient and may suffer from operator-to-operator variations. In other procedures, zygotes are processed one at a time and fluid flows are manually controlled, which are time-consuming and fraught with operator-to-operator variations. The new methods and systems described herein can avoid or overcome these problems in ART.

This disclosure provides microfluidic systems and methods for denuding oocytes from surrounding cumulus and corona cells with broad applications in the field of assisted human reproduction. At a general level, the systems include at least one channel having one or more stages, each stage having repeating constriction units and expansion units. A liquid sample, e.g., a raw follicular fluid sample, containing COCs can be injected into an inlet of the system, e.g., at a continuous flow rate. The flow rate causes the COCs to traverse through the channel of the system. The constriction units and the expansion units work together to facilitate the denudation of the oocytes. For example, the constriction units include surface features, such as smooth or jagged inner surfaces, for stripping or peeling the outer cells from the COCs. The expansion units promote tumbling of the COCs as they make their way through the system. The systems can be configured in such a manner that a continuous flow of COCs is achieved.

In other embodiments, the disclosure provides microfluidic systems and methods to denude oocytes from the surrounding cumulus cells while retrieving COCs from large volumes of liquid samples that may contain various sizes of debris. In some embodiments, an enzyme specific to cumulus cells, e.g., hyaluronidase, is added to a sample, e.g., a follicular fluid sample, to loosen COCs, but not other debris, and then the liquid sample is flowed through the systems described herein. The large debris, coagulated blood, etc. are captured in the channels and/or coarse filter upstream, while the COCs get denuded and go through the channels. This way the device removes the large debris while denuding the COCs so oocytes are collected at the exit of the systems. The new systems achieve the following objectives: 1) automatically denude oocytes from surrounding cumulus cells treated with an enzyme, e.g., hyaluronidase, to loosen the cumulus cells from the oocyte; 2) process a large volume of fluid suspension, such as follicular fluid, in a single operation without clogging; 3) selectively trap oversized blood clots and tissue debris; and 4) minimize human intervention with reduced processing time and improved standardization. In particular, the multi-channel systems capture large debris, coagulated blood, etc. in the coarse filters upstream and/or in the channels, while the COCs are denuded and can pass through the channels. Thus, the new systems remove the large debris while automatically denuding the COCs to yield oocytes at the outlet.

FIG. 1 is a schematic overview of the methods for using a microfluidic system 100, according to at least one embodiment of the present disclosure. The microfluidic system 100 can strip oocytes from their surrounding cumulus matrix in an automated and standardized manner. In general, a suspension of cumulus-oocyte complexes (COCs) 170a can be mixed with a buffer or culture medium. The medium is important for keeping the oocytes alive and healthy. In general, the suspension can have a volume of about 10 to 50 microliters. The mixture can encompass a total volume of about 500 microliters. In general, the mixture is prepared by adding the COC suspension to a container (e.g., a tube) filled with the culture medium (e.g., having a volume of up to about 500 microliters). The resulting liquid is injected into the microfluidic system 100 using, for example, a pump. The resulting liquid is injected into the microfluidic system 100, e.g., at a continuous flow rate. In various embodiments, the pump can be a motorized system like a syringe pump or a pressure-driven pump. In some embodiments, a vacuum can be pulled from the outlet to achieve the required flow rate.

In some implementations, the suspension includes debris of various sizes. For example, the suspension can include debris that is larger than the COCs and/or smaller than the COCs. In some implementations, the suspension is pre-incubated with an enzyme such as hyaluronidase before it is injected into the microfluidic system 100. For example, the suspension can be pre-incubated with 0.3 mg/mL hyaluronidase.

Careful selection of a continuous flow rate is important to the final outcome. For example, a flow rate that is too slow tends to hinder the movement of the mixture through the microfluidic system 100 and may render the device ineffective in denuding the oocytes. On the other hand, a flow rate that is too fast can cause the system 100 to damage the oocytes. As described herein, an optimal flow rate is between about 0.5 to about 2.0 ml/minute (0.5, 0.6, 0.7, 0.8, 0.9, 1.0, 1.1, 1.2, 1.3, 1.4, 1.5, 1.6, 1.7, 1.8, 1.9, or 2.0 ml/minute) and/or between about 3.0 ml/minute to about 5.0 ml/minute (3.0, 3.2, 3.4, 3.6, 3.8, 4.0, 4.2, 4.4, 4.6, 4.8, or 5.0 ml/minute) depending on the specific configuration of the microfluidic system used. As the COCs 170a make their way through the microfluidic system 100, the microfluidic system's 100 features apply mechanical forces to the COCs 170, facilitating the denudation of the COC's 170a cumulus cells. As the COCs 170a reach the end point of the microfluidic system 100, they become partially or completely denuded oocytes 170b. The denudated oocytes 170b are collected in an outlet reservoir of the microfluidic device 100.

System Overview

FIGS. 2A-2C are schematic illustrations of a microfluidic system 100 for removing cumulus cells from oocytes, according to the present disclosure. FIG. 2A shows the overall system, while FIGS. 2B and 2C show enlargements of several parts of the microfluidic system 100. Referring to FIG. 2A, the microfluidic system 100 includes an inlet 101, an outlet 102, a first stage 110, a second stage 120, and a third stage 130. Together, the first stage 110, second stage 120, and third stage 130, define a long serpentine channel. The inlet 101 is configured to receive COCs 170a and guide the COCs 170a to the first stage 110. The COCs 170a can be suspended and/or mixed with a buffer or culture medium. In this illustration, the long serpentine channel includes three "rows." The first (i.e., top) row includes the first stage 110 and the second stage 120, while the second and third (i.e. bottom) rows include the third stage 130. Although the channel is shown as serpentine, the channel can also be straight, circular, or various other shapes. The channel can also include more or fewer rows, depending on the desired use of the microfluidic system 100.

The serpentine channel is segmented into a series of repeated expansion units 140 alternating with smooth constriction units 141 and/or jagged constriction units 142. The shape and dimensions of these units 140, 141, 142 can change over the length of the channel. For example, in this particular illustration, the first stage 110 has square expansion units 140 while the second stage 120 and third stage 130 have octagonal expansion units 140. However each stage can include any number of various shapes of expansion units 140, to include square, octagonal, and/or round. In the embodiment shown, the first stage 110 includes twenty-five expansion units 140 and twenty-five smooth constriction units 141. The second stage 120 includes twenty-five expansion units 140 and twenty-five smooth constriction units 141. The third stage 130 includes one-hundred expansion units 140 and one-hundred jagged constriction units 142.

Also, in the shown embodiment, the first stage 110 and the second stage 120 are of equal lengths. However, the first stage 110 and the second stage 120 can have different lengths. In an embodiment, the length of the first and second stages 110,120 are about 10 to 50 mm, depending on the number of expansion and constriction units 140,141. The third stage 130 can be longer than the first two stages 110,120. In the shown embodiment, the third stage 130 is approximately four times longer than the first or second stage 110, 120. In the shown embodiment, the third stage 130 is about 40 to 200 mm in length.

Although FIG. 2A shows each stage having a particular arrangement of expansion units 140, smooth constriction units 141, and jagged constriction units 142, the microfluidic system 100 can include any number of stages that include various combinations of these units 140, 141, 142. For example, the second stage 120 can also include a number of jagged constriction units 142. The third stage 130 can include a number of smooth constriction units 141, which may or may not alternate between the jagged constriction units 142. The number and position of these units 140, 141, 142 can be optimized based on particular uses of the microfluidic system 100. The specific design of the stages 110, 120, 130 can be based on a desired function of the stages 110, 120, 130. For example, in the illustrated embodiment the configuration of the first and second stages 110, 120 facilitates the removal of the bulky, loosely attached cumulus cells of the COCs 170a. Also, in the illustrated embodiment, the configuration of the third stage 130 facilitates the removal of the corona radiata of the COCs 170a, which refers to the innermost layer of the cells directly adjacent to the zona pellucida.

The expansion units 140, smooth constriction units 141, and jagged constriction units 142 can have various heights. As described herein, a height refers to the distance between the "top" and "bottom" inner surfaces of the units 140, 141, and 142, according to how the units are oriented at a given time (with the understanding that a "top" can also be viewed as the "bottom," again, depending on how a unit is oriented in space at a given time). Thus, for example, the height can be a cross section (e.g., for squared or octagonal units) or a diameter (e.g., for circular units). In some embodiments, the expansion units 140, smooth constriction units 141, and the jagged constriction units 142 have heights between 150 to 500 microns. In some embodiments, the heights of all expansion units 140, smooth constriction units 141, and jagged constriction units 142 are constant. In some embodiments, the expansion units 140, smooth constriction units 141, and jagged constriction units 142 are configured to have heights large enough such that they can accommodate the size of the COCs without causing significant clogging of the channel. The units 140, 141, 142 can be configured to have a range of widths. For example, in certain embodiments the expansion units 140 have a width of 250 to 600 or more microns. Generally, the width of the expansion units 140 can be chosen to cause the COCs 170a to tumble such that the COCs' entire surface will contact the inner walls of the following constriction units 141, 142. In some embodiments, the smooth constriction units 141 are configured to have widths of 100 to 300 microns and the jagged constriction units 142 are configured to have widths of 90 to 130 microns. The units 140, 141, 142 can also be configured to have a range of lengths. For example, in certain embodiments, the expansion units 140 have lengths between 400-600 microns and the smooth and jagged constriction units 141, 142 have lengths of 550-750 microns.

FIG. 2B shows an enlargement of a curve 150 that transitions the second stage 120 to the third stage 130, which forms the second two rows of the long serpentine channel in this example. A curve 150 also transitions the second row to the third row, as shown in FIG. 2A.

FIG. 2C, shows an enlargement of a jagged constriction unit 142 positioned in the third stage 130. The jagged constriction units 142 include several jagged teeth 142a. As explained below with reference to FIG. 8A, the jagged teeth 142a can be set at one or more of several different angles either in or against the direction of flow through the channel. For example, in some embodiments, the jagged teeth 142a are set at an angle from about 30 degrees to about 90 degrees (e.g., 45, 50, 55, 60, 65, 70, 75, 80, or 85 degrees) against the direction of flow through the channel. In other embodiments, the jagged teeth 142a are set at an angle from about 40 degrees to about 150 degrees against the direction of flow through the channel.

The distance between the tips of the jagged teeth 142a can also vary. In general, the distance between the tips of the jagged teeth 142a is selected based on the average diameter of a human (or other animal, e.g., mammalian) oocyte (e.g., 100 microns) and therefore is set to be between about 80 and 110 microns. The distance between the tips of the jagged teeth 142a can be set at several distances, however it is preferable to set the distance between the tips of the teeth 142a such that they can facilitate denudation without causing excessive damage to the oocyte. For example, if the distance between the tips of the teeth 142a is too small, the oocyte might not be able to squeeze between them without damage. If the distance between the tips of the teeth 142a is too large, then the teeth 142a may not be able to remove the cumulus cells from the COC 170a. The distance between the tips of the teeth 142a can be at least partially defined by the length of the teeth 142a. Consequently, each of the jagged teeth 142a can be configured to have one of several lengths. For example, in some embodiments, the jagged teeth 142a are about 0.5 to 20 microns in length (e.g., 1, 2, 3, 4, 5, 10, 15, or 20 microns in length).

The microfluidic system 100 can be made of a substrate of polydimethylsiloxane (PDMS) or other hard, inert plastic or other material, and the substrate once etched or otherwise cut, using standard techniques, to form the channel in the substrate is bonded to a cover, such as a glass slide, to provide a water-tight seal. When choosing the substrate and cover materials, it is important that they be compatible and biologically inert, so as not to harm the oocytes passing through the channel.

Constriction and Expansion Units

FIG. 3A shows an enlargement of a smooth constriction unit 141 and proximate expansion units 140 located in the first stage 110 of the microfluidic system 100, according to an embodiment of the present disclosure. FIG. 3B shows an enlargement of a smooth constriction unit 141 and proximate expansion units 140 located in the second stage 120 of the microfluidic system 100, according to an embodiment of the present disclosure. FIG. 3C shows an enlargement of a jagged constriction unit 142 and proximate expansion units 140 located in the third stage 130 of the microfluidic system 100, according to an embodiment of the present disclosure.

As shown in FIG. 3A, the smooth constriction unit 141 is proceeded and followed by expansion units 140. In this embodiment, the expansion units 140 of the first stage 110 are rectangular shaped and have a width $W_0$. In this embodiment, the width $W_0$ is about 500 microns, however the width $W_0$ can be one of several other sizes, as discussed earlier with reference to FIGS. 2A-2C. In all three stages 110, 120, 130, the expansion units 140 can facilitate the tumbling of COCs such that substantially the entire surface of the COCs can interact with the inner surfaces of the following smooth constriction units 141 or jagged constriction units 142. The smooth constriction unit 140 includes smooth inner surfaces, which generally refers to a surface that lacks jagged teeth and other roughness or protrusions that could insert into the cumulus layers surrounding the oocytes. The smooth constriction unit 141 of the first stage 110 also has a width $W_1$. In this illustrative embodiment, the width $W_1$ is about 240 microns, which can facilitate the removal of the large, loosely attached cumulus clusters presented in the COC. However, the width $W_1$ can be one of several other sizes, as discussed earlier with reference to FIGS. 2A-2C. Also, as indicated earlier with reference to FIGS. 2A-2C, the first stage 110 can include one or more jagged constriction units 142 in addition to, or in lieu of, the smooth constriction units 141.

As shown in FIG. 3B, the smooth constriction unit 141 of the second stage 120 has a width $W_2$. The smooth constriction unit 141 of the second stage 120 can have a width $W_2$ that is smaller than the width $W_1$ of the smooth constriction unit 141 of the first stage 110. However, the width $W_2$ of the second stage's 120 smooth constriction unit 141 can be larger or equal to the width $W_1$ of the first stage's 110 smooth constriction units 141. In some embodiments, the width $W_2$ is chosen to facilitate the removal of intermediate sized cumulus clusters that may not have been removed by the smooth constriction units 141 of the first stage 110. In this illustrative embodiment, the width $W_2$ is about 140 microns, and thus is smaller than the width $W_1$ of the smooth constriction units 141 of the first stage 110. However the width $W_2$ can be one of several other sizes, as discussed earlier with reference to FIGS. 2A-2C. The smooth constriction unit 141 of the second stage 120 also has smooth inner surfaces. The smooth constriction unit 141 is preceded and followed by expansion units 140.

The expansion units 140 of the second stage 120 are octagonal in shape. However, the expansion units 140 of the second stage 120 can also be square shaped or round shaped. Octagonal and/or rounded shaped expansion units 140 can prevent the formation of vortices that may be seen in the four corners of square shaped expansion units 140. The expansion units 140 of the second stage 120 also have a width $W_0$ of 500 microns. However, the expansion units 140 of the second stage 120 can have widths larger or smaller than the widths $W_0$ of the first stage's 110 expansion units 140. For example, in an embodiment, the expansion units 140 of the second stage 120 have widths larger than the widths $W_0$ of the expansion units 140 of the first stage 110. In the present embodiment, the expansion units 140 of the second stage 120 have widths smaller than the widths $W_0$ of the first stage's 110 expansion units 140, but larger than the widths $W_2$ of the smooth constriction units 141 of the second stage 120.

As shown in FIG. 3C, the jagged constriction unit 142 of the third stage 130 has a width $W_3$. The width $W_3$ of the jagged constriction unit 142 is generally smaller than the width $W_2$ of the smooth constriction unit 141 of the second stage 120. For example, in this illustrative embodiment, jagged constriction unit 142 has a maximum width $W_3$ of 130 microns. However the width $W_3$ can be one of several other sizes, as discussed earlier with reference to FIGS. 2A-2C. The jagged constriction unit 142 includes a plurality of jagged teeth 142a. The plurality of jagged teeth 142a are angled towards the continuous flow (indicated by the bold arrow pointed towards the right) of the serpentine channel. The jagged constriction unit 142 is preceded and followed by expansion units 140. The expansion units 140 of the third stage 130 also have a width $W_0$, which is equal to that of the expansion units 140 in the other stages. However, similar to the expansion units 140 of the second stage 120, the expansion units 140 of the third stage 130 can have widths smaller or larger than the widths $W_0$ of the other stages' 110, 120 expansion units 140. In the embodiments illustrated in FIGS. 2B, 2C, and 3A-3C, the widths of the constriction units 141, 142 are smaller at each successive stage. For example, the smooth constriction units 141 of the first stage have a width $W_1$ that is larger than the width $W_2$ of smooth and/or jagged constriction units in the second stage 120, which, in turn, have larger widths ($W_2$) than the widths $W_3$ of the jagged constriction units 142 of the third stage 130. This can facilitate the gradual removal of the cumulus layers from the COCs. By allowing for a more gradual approach to cumulus layer removal, the design of the illustrated embodiment can prevent potential clogging between the stages while easing the workload for each following stage.

In some implementations, the microfluidic system 100 includes multiple channels arranged e.g., in parallel (e.g., each channel including the first stage 110, second stage 120, and third stage 130 for denuding the COCs 170a), such that a liquid sample including several COCs 170a can flow through the multiple channels. The multiple channels can be formed on the same or on different substrates, and can be connected in parallel, e.g., using conduits or manifolds that connect the various inlets together to a main inlet and the various outlets together to a main outlet of the system. Including multiple channels in parallel can facilitate a continuous flow of COCs 170a should one channel become defective or clogged.

Microfluidic Systems Having a Channel with Multiple Sub-Channels

Figures 4A, 4B, 4C:
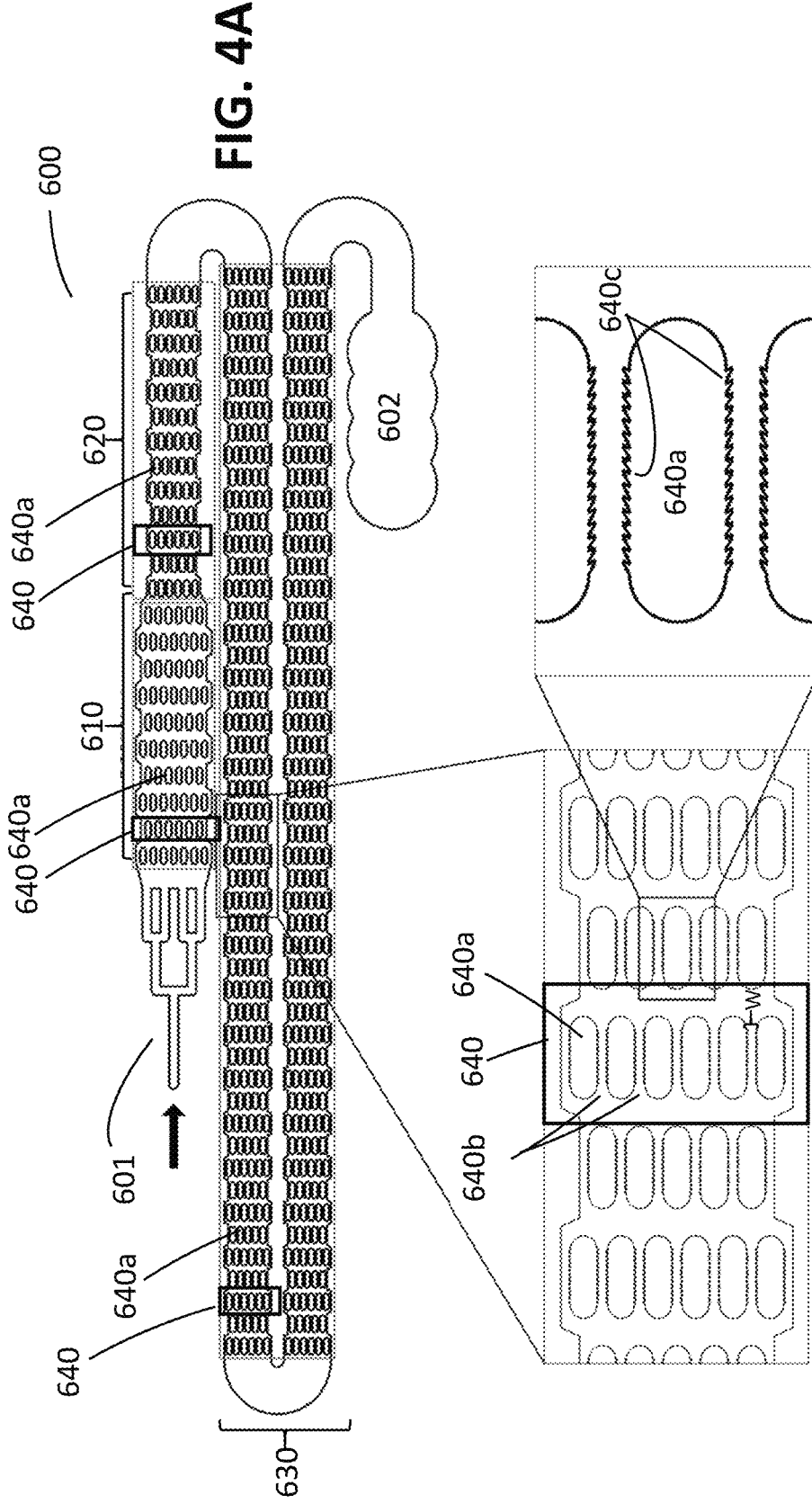
FIGS. 4A-4C are schematic illustrations of a microfluidic system having a channel including multiple sub-channels defined by rows of posts within the channel for removing cumulus cells from COCs, according to an embodiment of the present disclosure.

FIGS. 4A-4C are schematic illustrations of a microfluidic system 600 having a channel with multiple sub-channels for removing cumulus cells from COCs, according to an embodiment of the present disclosure. The microfluidic system 600 having multiple sub-channels can be used, for example, when the liquid sample containing the COCs may also contain additional debris that can block or clog a single channel. The various sub-channels can provide various paths for the COCs to flow through in the event one path becomes blocked or clogged.

FIG. 4A shows the overall system, while FIGS. 4B and 4C show enlargements of several parts of the microfluidic system 600. Referring to FIG. 4A, the microfluidic system 600 includes an inlet 601, an outlet 602, a first stage 610, a second stage 620, and a third stage 630. Together, the first stage 610, second stage 620, and third stage 630, define a long serpentine channel. In this illustration, the long serpentine channel includes three sections. The first (i.e., top) section includes the first stage 610 and the second stage 620, which are both filtering stages that help remove debris from the liquid sample, while the second and third (i.e. bottom) sections include the third stage 630, which provides the denuding effect. Although the channel is shown as serpentine, the channel can also be straight, circular, or various other shapes. The channel can also include more or fewer sections, depending on the desired length and/or use of the microfluidic system 600.

The serpentine channel includes a plurality of rows 640 of posts 640a. Each row 640 includes a plurality of posts 640a. The shape and dimensions of these posts 640a can remain constant or change over the length of the channel. For example, in this particular illustration, the first stage 610, second stage 620, and third stage 630 include oval-shaped posts 640a. However, each stage can include any number of various shapes of posts 640a, to include square, rectangular, and/or octagonal posts. Each stage can also include any number of rows 640 of posts 640a, and each row 640 can have any number of posts 640a. In the embodiment shown, the first stage 610 includes several rows 640 that have seven posts 640a and several rows 640 that have six posts 640a. The second stage 620 includes several rows 640 that have six posts 640a each, and several rows 640 that have five posts 640a each. The third stage 630 includes several rows that have six posts 640a each and several rows 640 that have five posts 640a each. In all embodiments, the rows of posts are arranged across the channel, e.g., perpendicular to a longitudinal axis of the channel, or at an angle, e.g., a slight angle, to the longitudinal axis of the channel.

The first stage 610, second stage 620, and third stage 630 can all have equal lengths or different lengths. In some implementations, the length of the first and second stages 610, 620 are about 10 to 50 mm, depending on the number of rows 640 of posts. The third stage 630 can be longer than the first two stages 610, 620. In the embodiment shown, the third stage 630 is approximately four times longer than the first or second stage 610, 620. In various embodiments, the third stage 630 can be about 40 to 200 mm in length. In one embodiment, each post can be about 800 microns long, and the system can include about 100 of these posts in the third stage to achieve effective denudation. The horizontal distance between rows of posts can be about 400 microns, but this distance is not critical and can vary as long as the COCs have sufficient space and time between rows of posts to tumble or rotate. For example, in this embodiment the third stage can be a total of 120 mm in length.

An important parameter is the total length of jagged surface, when counting all of the posts along a sub-channel, and in the above embodiment, this is about 80 mm. A shorter length of jagged surface for each post is possible, but then more posts would be required in the third stage. Alternatively, one can have a longer length of jagged surface for each post and include fewer posts in the third stage. However, the total length of jagged surface in the third stage should be more than about 80 mm. The total length of jagged surface can also be longer, e.g., 100 mm, 120 mm, or 150 mm, but if the total length of jagged surface is too long, the oocytes may become unduly damaged.

FIG. 4B shows an enlargement of a row 640 of posts positioned in the third stage 630. Each post 640a in a given row 640 is spaced apart from a neighboring post 640a to define a sub-channel 640b having a width (W). The posts 640a at the ends of the row 640 are spaced apart from the walls of the channel to define additional sub-channels 640b. The width of these sub-channels can be between about 80 and 110 microns, e.g., 80, 85, 90, 95, 100, 105, or 110 microns, which is based generally on the diameter of the oocytes to be denuded.

The first stage 610, second stage 620, and third stage 630 can all include post rows 640 having sub-channels 640b with equal widths (W) or varying widths (W). In the embodiment shown, each sub-channel 640b in the first stage 610 has a width (W) of 240 microns, each sub-channel 640b in the second stage 620 has a width (W) of 140 microns, and each sub-channel 640b in the third stage 630 has a width (W) of 90 microns.

FIG. 4C shows an enlargement of a few posts 640a positioned in the third stage 630. Each post 640a includes a plurality of jagged teeth 640c along an elongate wall of the post. The jagged teeth 640c can be set at one or more of several different tilting angles either in or preferably against the direction of flow through the sub-channel. For example, in some embodiments, the jagged teeth 640c are set at an angle from about 30 degrees to less than about 90 degrees against the direction of flow through the channel. The distance between the tips of the jagged teeth 640c can also vary, but in general the distance between the tips of the jagged teeth 640c is selected based on the average diameter of a human (or other animal, e.g., mammalian) oocyte (e.g., 100 microns) and therefore is set to be between about 80 and 110 microns.

The distance between the tips of the jagged teeth 640c can be set at several different distances; however, it is preferable to set the distance between the tips of the teeth 640c such that they can facilitate denudation without causing excessive damage to the oocyte. For example, if the distance between the tips of the teeth 640c is too small, the oocyte might not be able to squeeze between them without damage. If the distance between the tips of the teeth 640c is too large, then the teeth 640c may not be able to remove the cumulus cells from the COCs. The distance between the tips of the teeth 640c can be at least partially defined by the length of the teeth 640c. Consequently, each of the jagged teeth 640c can be configured to have one of several lengths. For example, in some embodiments, the jagged teeth 640c are about 0.5 to 20 microns in length (e.g., 1, 2, 3, 4, 5, 10, 15, or 20 microns in length).

In the embodiment shown in FIGS. 4A-4C, every post 640a within all of the stages 610, 620, 630 includes jagged teeth 640c. However, any of the stages can additionally, or alternatively, include any number of smooth posts 640a. Furthermore, the jagged teeth 640c of each post 640a in each stage can include various lengths and spacing between tips. In addition, although the walls of the serpentine channel are smooth in this embodiment, any or all of the stages 610, 620, 630 can include walls that also have jagged teeth 640c.

The specific design of the stages 610, 620, 630 can be based on a desired function of the stages 610, 620, 630. For example, in the illustrated embodiment, the configuration of the post rows 640 of the first and second stages 610, 620 facilitates the removal of the bulky, loosely attached cumulus cells of the COCs flowing through the sub-channels 640b, while capturing large debris that is included within the liquid sample. In addition, in the shown embodiment, the configuration of the third stage 630 facilitates the removal of the corona radiata of the COCs flowing through the channel, while capturing smaller debris that is including with the liquid sample.

Although each stage of the shown embodiment includes several rows 640 of posts, any or all of the stages can include only one row of posts having several elongated posts 640a. However, having multiple rows 640 with some spacing between each row 640 can facilitate more efficient denuding, as the spaces between the rows of posts facilitate the rotating of the COCs flowing through the channel.

Figure 9:
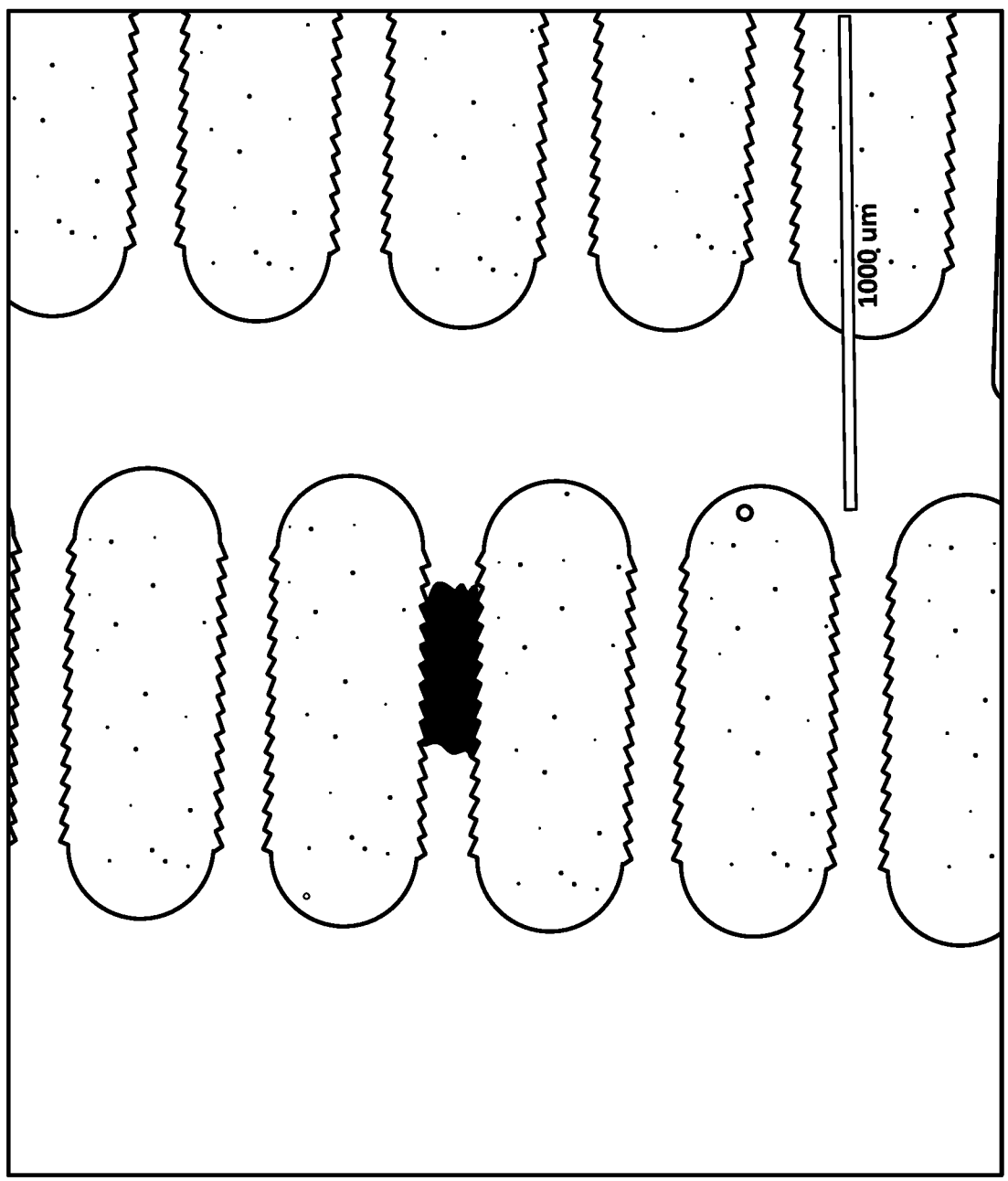
FIG. 9 is a representation of a magnified image that shows debris being captured in a sub-channel of a microfluidic system having multiple sub-channels defined between oval posts aligned in rows.

FIG. 9 is a representation of a magnified image that shows debris being captured by a sub-channel of a microfluidic system. As shown, the various sub-channels 640c of the microfluidic device 600 can capture debris that may be included within the liquid sample, and the COCs of the sample can flow through the other sub-channels 640 for denudation.

Methods of Use

Figure 5:
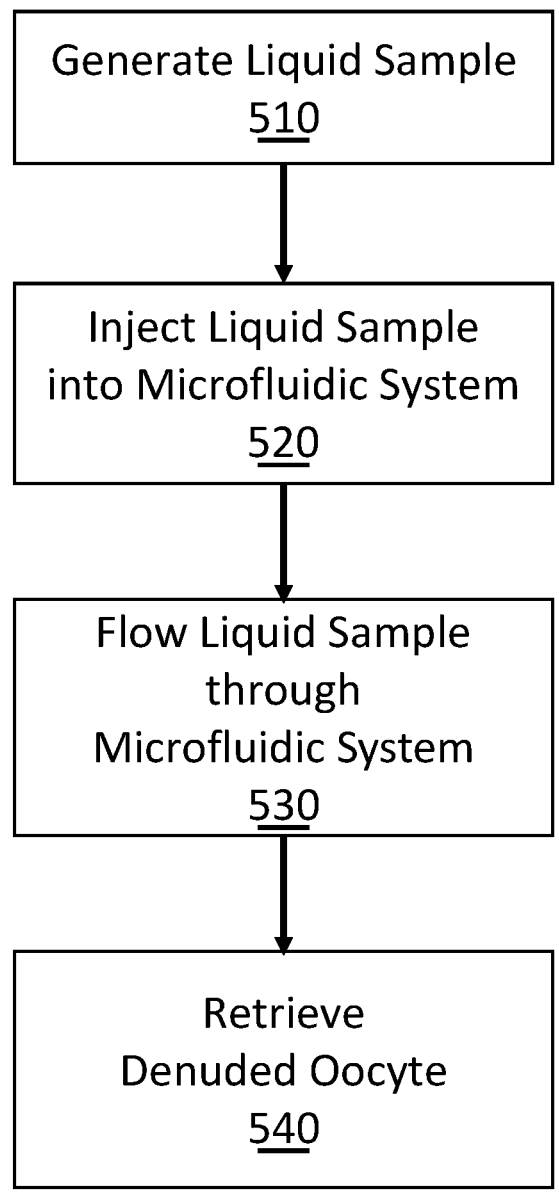
FIG. 5 is a flow chart showing an example of a method of using the microfluidic systems described herein, according to at least one embodiment of the present disclosure.

FIG. 5 is a block diagram showing a method of using the microfluidic system 100 according to at least one embodiment of the present disclosure. For illustrative purposes, the method will be described as being used with the microfluidic system 100 discussed previously with reference to FIGS. 2A-2C. However, the method can be used with other microfluidic systems, such as the microfluidic system 600 having multiple sub-channels discussed previously with reference to FIGS. 4A-4C. The method includes generating a liquid sample (block 510), injecting the liquid sample into the microfluidic system 100 (block 520), flowing the liquid sample through the microfluidic system 100 (block 530) and retrieving the denuded oocyte (block 540).

At block 510, a suspension containing COCs 170a is loaded into a tubing, which can be pre-filled with culture media. In some embodiments, the tubing is pre-filled with a buffer. The suspension of COCs 170a is mixed with the culture/buffer medium to generate a liquid sample. The liquid sample can have a total volume of about 300-700 microliters. In some embodiments, the liquid sample encompasses a total volume of about 500 microliters. In some embodiments, the suspension includes debris of various sizes. For example, the suspension can include debris that is larger than the COCs and/or smaller than the COCs. In some implementations, the suspension is pre-incubated with hyaluronidase before it is injected into the microfluidic system. For example, the suspension can be pre-incubated with 0.3 mg/mL hyaluronidase. Incubating the suspension with hyaluronidase can facilitate removal of the cumulus cells by loosening the bonds between the cumulus cells of the COCs.

At block 520, the tubing is connected to a pump, e.g., to a syringe controlled by a pump, e.g., by a needle. The syringe is mounted on a pump that can apply a constant flow rate. The other end of the tubing is plugged into the inlet 101 of the microfluidic system 100. The liquid sample containing the COCs 170a is then injected into the inlet 101 of the microfluidic system 100 at the constant flow rate. The constant flow rate can be between 0.1-2.0 mL/min. In some embodiments, the constant flow rate is 0.5 mL/min. In other embodiments, the constant flow rate is 0.75 mL/min or 1 mL/min.

When using the microfluidic system 600 having multiple sub-channels as discussed herein with reference to FIGS. 4A-4C, a higher constant flow rate can be used due to the many sub-channels. In some embodiments, the constant flow rate is between 3 mL/min to 5 mL/min.

At block 530, the pump-flow action causes the liquid sample to flow through the microfluidic system 100. As the liquid sample flows through the microfluidic system 100, the COCs pass through the several expansion units 140, smooth constriction units 141, and jagged constriction units 142 of the microfluidic system 100. In general, the expansion units 140 are designed to cause the COCs 170a to tumble, which helps as much of the surface of the COCs as possible to contact the inner walls of the following constriction channels 141, 142. In general, the smooth constriction units 141 facilitate the removal of the bulky, loosely attached cumulus cells of the COCs 170a, and the jagged constriction units 142 facilitate the removal of the corona radiata of the COCs 170a.

Figure 6B:
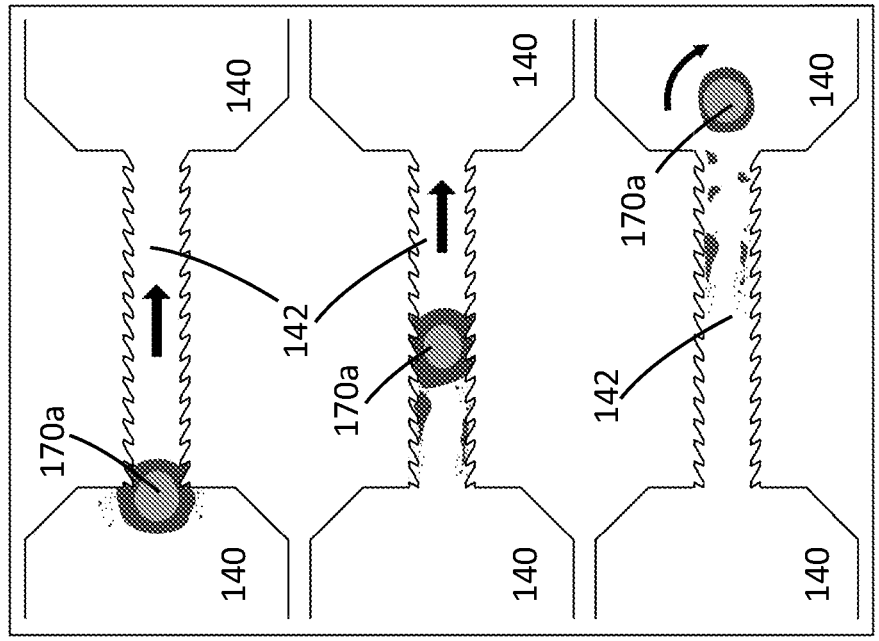
FIG. 6B is a schematic illustration that shows a COC flowing through a single jagged constriction unit, according to at least one embodiment of the present disclosure.
Figure 6A:
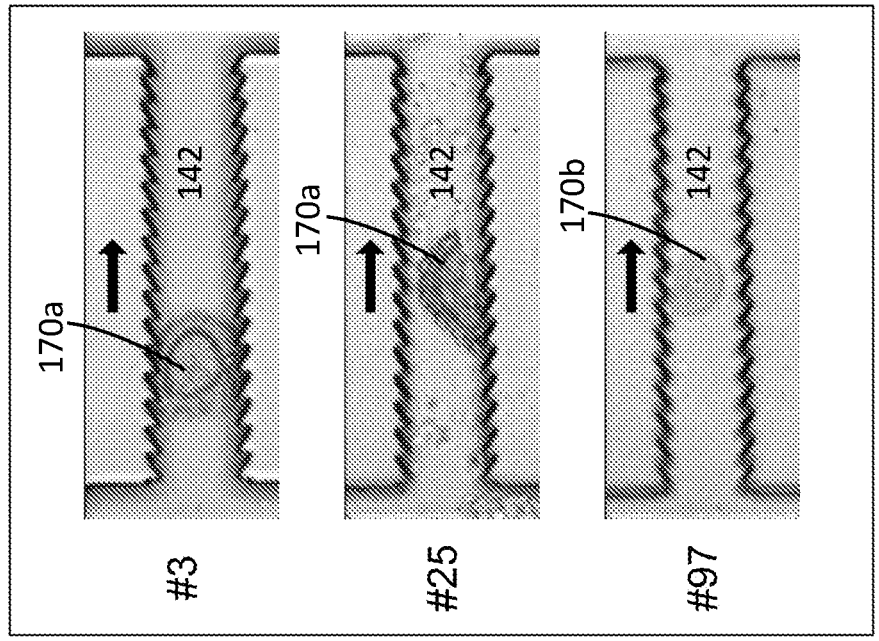
FIG. 6A is a representation of a magnified image that shows a COC flowing through three separate jagged constriction units, according to at least one embodiment of the present disclosure.

For example, FIG. 6B shows a COC 170a flowing through a jagged constriction unit 142. The constriction unit includes jagged teeth angled towards the flow of the COC 170a, the flow being indicated by the bold arrows pointing to the right. As the COC 170a traverses the jagged constriction unit 170a, the jagged teeth apply shear stress on the COC 170a, facilitating the denudation of the oocyte in the COC 170a. As the COCs 170a make their way through the microfluidic system 100, the COCs 170a become more and more denuded. For example, FIG. 6A shows a COC 170a flowing through three separate jagged constriction units 142 numbered 3, 25, and 97, respectively. The top jagged constriction unit 142 represents the third jagged constriction unit 142 in the third stage 130 of the microfluidic system 100. The middle jagged constriction unit 142 represents the twenty-fifth jagged constriction unit 142 in the third stage 130 of the microfluidic system 100. The bottom jagged constriction unit 142 represents the ninety-seventh jagged constriction unit 142 in the third stage 130 of the microfluidic system 100. As shown, the COC 170a becomes more and more denuded as it traverses through each jagged constriction unit 142. When the COC 170a passes through the final series of jagged constriction units 142, the oocyte has become mostly or completely denuded.

Referring back to FIG. 5, when using the microfluidic system 600 having multiple sub-channels as discussed previously with reference to FIGS. 4A-4C, the COCs can pass through the multiple sub-channels 640c of the rows 640 of posts. The sub-channels 640c are configured to remove the cumulus cells of the COC in a similar manner as the constriction units 142 (e.g., by applying mechanical force to the cumulus cells).

At block 540, after the COCs 170a are processed through the series of units 140, 141, 142, the COCs 170a become fully denuded oocytes 170b. However, the COCs 170a can become only partially denuded oocytes 170b based on the particular design and intended use of the microfluidic system 100. The partially/fully denuded oocytes 170b are collected at the outlet 102 (i.e., outlet reservoir 102) of the microfluidic system 100.

EXAMPLES

The invention is further described in the following examples, which do not limit the scope of the invention described in the claims.

Example 1—Operation of a Microfluidic Oocyte Denuding System

A 10-µl suspension containing about 7-12 mouse COCs pre-incubated with 0.3 mg/mL hyaluronidase was transferred into a Tygon® tubing prefilled with 0.5 ml of culture media. The tubing had an inner diameter of about 1.27 mm. One end of the tubing was connected to a syringe pump through a 15-gauge blunt needle. The pump applied a constant flow rate of 1 ml/min. The other end of the tubing was inserted into the microfluidic system's inlet. The sample was then injected into a microfluidic system as described herein. The microfluidic system was bonded to a single 75 mm×25 mm glass slide. The microfluidic system had three stages, with the third stage having constriction unit widths of either 80, 90, 100, 110, 120, 130, or 140 µm. Within 30 seconds, the processed oocytes were collected in the outlet reservoir. A yield was calculated as the number of processed oocytes out of the total COCs transferred into the tubing. An efficiency was calculated as the proportion of denudated oocytes out of the total processed oocytes that are collected in the outlet reservoir.

Figure 7:
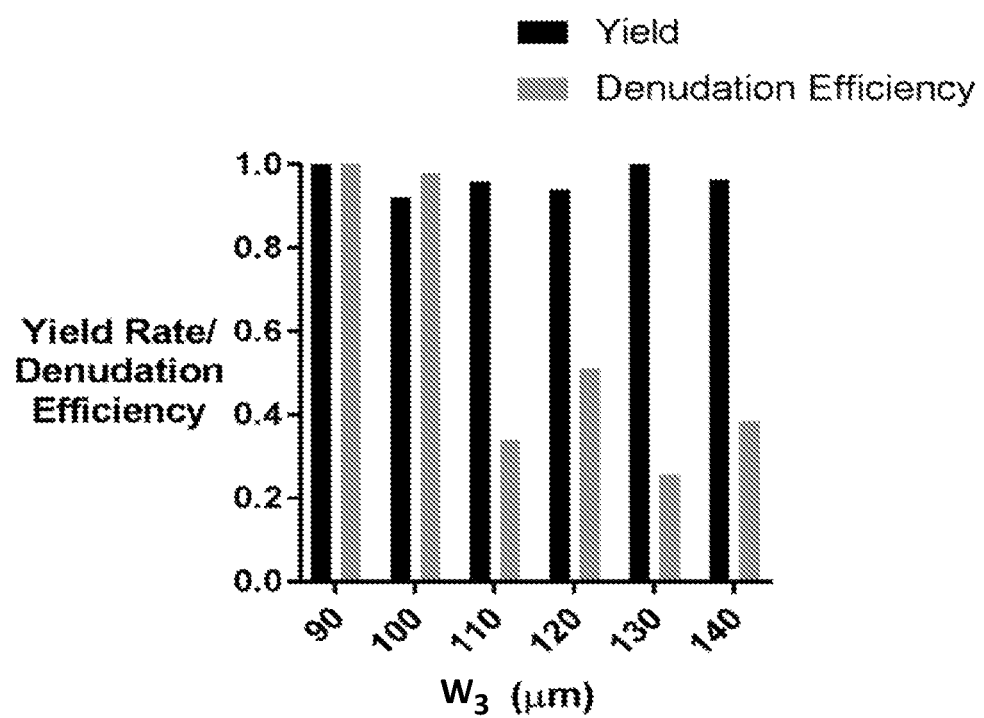
FIG. 7 is a bar graph that shows the effect of the stage three constriction units' width ($W_3$) on the yield rate and denudation efficiency for the processed COCs.

FIG. 7 is a bar graph that shows the effect of the stage three constriction width ($W_3$) on the yield rate and denudation efficiency for the processed COCs. As shown, the denudation efficiency was at or near 100% for widths of 90 and 100 microns, but dropped off sharply at widths over 100 microns. Although not shown, the efficiency was also 100% for a width of 80 microns, but the typical mouse oocyte is about 90 microns in diameter, and it is important that a distance between the tips of the teeth in the third stage constriction units be no smaller than the approximate width of the oocyte to avoid damaging the oocytes. Thus, a useful distance between the tips of the teeth in the third stage constriction units for mouse oocytes is about 90 to 100 microns in this system. Human oocytes typically have a width of about 100 microns, and thus a useful distance between the tips of the teeth in the third stage constriction units for a human oocyte in the microfluidic system is about 100 to 110 microns.

Example 2—Selection of Geometry and Flow Parameters

Germinal-vesicle (GV) stage oocytes and their associated COCs were used in the denudation devices. GV stage COCs feature an unexpanded, compact cumulus-corona cell mass while metaphase II (MII) stage COCs have an expanded, less compact cumulus-corona cell mass with corona cells radiating away from the zona pellucida. Mouse MII stage COCs typically form a large cluster. The optimized parameters obtained with GV stage COCs were used on mature, MII stage COCs for in vitro fertilization experiments.

Using GV stage COCs, three major parameters were adjusted to achieve complete denudation of GV stage oocytes. The three major parameters were: the width ($W_3$) of jagged-surface constriction units, the total number (N) of constriction-expansion units in the third section, and the flow rate (Q) that the syringe pump applied. Yield rate was calculated as the percentage of completely or incompletely denuded oocytes retrieved in the outlet reservoir of the microfluidic system. Denudation efficiency was calculated as the percentage of completely denuded oocytes out of the total number of oocytes retrieved in the outlet reservoir. Almost 100% of the oocytes from COCs that entered the device were recovered in the outlet reservoir, independent of $W_3$, N, and Q. It is possible that some oocytes or COCs may stick to the hydrophilic inner surface of the tubing. When N=100 and Q=1 mL/min, the mean denudation efficiency decreased from 98.6% to 26.7% as $W_3$ increased from 90 to 130 μm.

These results indicate that it is important for the narrowest constriction width ($W_3$) to be close to the average size of the cumulus-free oocyte (i.e., ~90 μm in diameter) to perform denudation, which highlights that the physical contact between COCs and the inner wall is essential.

In addition to the width $W_3$, the effects of N and Q were also monitored. In the case of $W_3$=90 μm and Q=1 mL/min, the denudation efficiency decreased dramatically to 28.3% when the number of constriction-expansion units in the third section (N) was reduced to 50. These results imply that configuring the microfluidic system to have adequate constriction-expansion units, such that the entire surface of a given COC has the chance to contact the inner wall of the constriction channel, is important for the complete denudation of oocytes.

Although the contact of COCs with the jagged-surface inner wall is important, it alone may not guarantee complete denudation of oocytes. When the flow rate was reduced to 0.5 mL/min, the denudation efficiency was 22.2%. Even a flow rate of 0.75 mL/min generated a lower denudation efficiency (86.2%) than a flow rate of 1 mL/min (98.6%). Therefore, in addition to sufficient physical contact, it is important for the shear stress to be directly correlated with the flow rate to be large enough to strip off the cumulus-corona cell mass. To explore the effect of shear stress, computational fluid dynamics (CFD) simulations of the fluid flow within the device or through the capillary tip during the manual pipetting was conducted. The maximum shear stress was directly correlated with the flow rate.

For fluid flow through repeating constriction-expansion units, on one hand, the maximum shear ($\tau_{max}$) increased from 64.1 to 163.5 Pa as the flow rate increased from 0.5 to 1 mL/min. The maximum shear occurred at the first pair of teeth after entering the jagged-surface constriction channel. On the other hand, $\tau_{max}$ increased from 149.8 to 392.0 Pa as the flow rate generated by manual pipetting increased from 0.5 to 1 mL/min. For manual pipetting, the maximum shear occurred at the inner ring of the capillary tip. The glass capillary used for denudation can have an outer diameter of 200 μm and an inner diameter of 125 μm. The typical flow rate applied by many embryologists can range from 500 to 750 μL/min as estimated from a video recording at 60 frames/second. Manual pipetting can apply different shear stress in each up-and-down cycle due to the variation in flow rate, which can generate a difference in the maximum shear stress of up to 250 Pa between 0.5 and 1 mL/min. However, the microfluidic device was able to keep the shear stress constant due to the constant flow rate applied. The maximum difference in shear stress between on-chip and manual denudation can be as much as 230 Pa in the case of a flow rate of 1 mL/min.

To validate the CFD simulation results, the shear stress acting on the inner wall of the glass capillary in the fully developed flow region was predicted. The shear stress acting on the inner wall at the location that is 2,500 μm from the capillary tip axially was 44.9, 65.5, and 82.5 Pa under a flow rate of 0.5, 0.75, and 1 mL/min, respectively. The shear stress ($\tau$) at this location can also be calculated theoretically based on the Poiseuille's law, $$\tau = \frac{4\mu Q}{\pi r^3},$$

where μ is the dynamic viscosity of the fluid (i.e., water), Q the flow rate, and r the inner radius of the capillary. The theoretical calculation obtained the shear stress of 38.7, 58.0, and 77.4 Pa at a flow rate of 0.5, 0.75, and 1 mL/min, respectively. This result was in good agreement with the CFD simulation results, which demonstrated the accuracy of the simulation models.

When MII stage mouse COCs are ovulated, they form a single, tight cluster in the oviduct. The cluster can loosen after 5 minutes of incubation with 0.3 mg/mL hyaluronidase at 37° C. To evaluate the performance of the microfluidic system under a condition close to typical ART clinics, denudation experiments on MII stage mouse COCs were conducted. The denuded oocytes were then used in IVF and ICSI experiments to examine their fertilization and developmental potential. The microfluidic system featuring $W_3=90$ μm and $N=100$ was sufficient to achieve complete denudation when the hyaluronidase-treated cluster of MII stage COCs traversed the system at a flow rate of 1 mL/min. The mean yield rate was 98.9% and the denudation efficiency was 93.7% on average. It was observed that, because the closely packed clusters of MII stage COCs were loosened to varying degree after hyaluronidase incubation, the need to break the clusters into individual COCs can reduce the denudation efficiency as compared with the denudation of GV stage COCs, which can typically be isolated complexes. It should be noted that typical clinical human samples may not have such clusters, even in the MII stage.

Example 3—Selection of Tilt Angle of Jagged Teeth

To investigate how the surface features of the constriction units affect the denudation performance, various tilting angles θ were introduced into the systems. The "tilting angle" refers to the angle between the flow direction of the COCs and the median line of the constriction units' jagged teeth. FIG. 8A is an illustration of four different tilting angles of jagged teeth tilting along a constriction channel. As shown in in FIG. 8A, as θ increased from 0° to 141°, the teeth of the jagged-surface inner wall changed from tilting along and in the flow direction of the COCs to tilting against the flow direction of the COCs. FIGS. 8B and 8C show the yield rate and denudation efficiency of the microfluidic system featuring different tilting angles θ.

As shown, the yield rate appears to be independent of the titling angle θ. However, it appeared that the jagged teeth featuring a tilting angle θ>90° may be able to "shave" off the corona cells completely. Therefore, based on these results, the most effective tilting angle θ range is 90°<θ<180°, meaning the range at which the teeth are tilting against the flow direction of the COCs. It should be noted that the flow rate was 1 mL/min and the microfluidic system had 100 repeating constriction-expansion units in the third section with a constriction unit width $W_3=90$ μm. It was also observed that the effect of the tilting angle θ may not be related to the shear stress. CFD simulations estimated that the maximum shear stress was 145.3 and 163.5 Pa for θ=39° and 141°, respectively. In both cases, the maximum shear stress acted at the first tooth when entering the constriction units. There may have also existed a minimal difference in shear stress at tilting angles between θ=39° and 141° for the rest of the teeth along the constriction unit. The shear stress was 84.1 Pa for the second to last tooth when the tilting angle θ=39° and was 94.7 Pa when the tilting angle θ=141°. The shear stress may therefore not have been responsible for the difference in denudation efficiency. Thus, it may be more important to denudation efficiency that the teeth are tilted against the flow direction of the COCs (e.g., θ=141°) such that the jagged teeth can strip, peel, or otherwise shave off the cumulus cells when the cumulus layers fill up the space between the teeth.

To further examine the role of the expansion units in oocyte denudation, we designed a microfluidic system in which 100 constriction channels in the third section were connected end to end without any expansion channels in between. This microfluidic system had the same first and second sections as those discussed previously with reference to FIGS. 2A-2C. Although the yield rate was close to 100%, the denudation efficiency in the absence of repeating expansion units became less than 20%. Thus, expansion units, which promote the tumbling of COCs, are important with respect to denudation efficiency. Furthermore, the COCs processed by the microfluidic system typically have an appearance of exposed zona pellucida on one or two sides and cumulus-corona cells remaining intact on the other sides in a two-dimensional image. This may suggest only certain parts of the COC surface get physical interaction with the inner wall rather than the entire surface in the absence of expansion units.

Example 4—Using Multiple Sub-Channels

A microfluidic system having multiple sub-channels, similar to the microfluidic system 600 discussed above with reference to FIGS. 4A-4C, was used to denude COCs suspended in a liquid sample. The suspension contained COCs and debris of various sizes. The suspension was pre-incubated with 0.3 mg/ml hyaluronidase to loosen the cumulus cells from the oocytes. The suspension was caused to flow through the microfluidic system at flow rates between 3 mL/min to 5 mL/min. The first stage of the system included sub-channels having a width of 240 microns. The second stage of the system included sub-channels having a width of 140 microns. The third stage of the system included sub-channels having a width of 90 microns. Every stage included posts having jagged teeth tilting against the direction of fluid flow.

FIG. 10 is a graph that shows the effect of flow rate on the yield rate and denudation efficiency of the microfluidic system having multiple sub-channels. As shown, the flow rate of 5 mL/min resulted in the highest yield (i.e., the number of oocytes collected at the outlet per number of oocytes entering the inlet) and denudation efficiency (i.e., the number of successfully denuded oocytes per number of oocytes collected at the outlet).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A system for denuding oocytes from attached cumulus cells, comprising:
   a substrate; and
   a channel comprising an inlet, an outlet, and one or more stages arranged in series between the inlet and the outlet,
   wherein each stage is in fluid communication with a subsequent stage,
   wherein each stage comprises one or more expansion units alternating with one or more constriction units, and
   wherein at least one of the stages comprises one or more of the constriction units, wherein each of these constriction units have two opposing walls, wherein each of the two opposing walls comprises a jagged internal surface comprising a plurality of teeth, wherein the plurality of teeth on a first opposing wall are pointed towards the plurality of teeth on a second opposing wall, and wherein all of the plurality of teeth are tilted against a direction of flow through the channel at a tilting angle of from about 30 degrees to less than 90 degrees, wherein the tilting angle is an angle between the direction of flow and a median line of the individual teeth in the plurality of teeth.

2. The system of claim 1, wherein tips of the plurality of teeth on the first opposing wall and tips of the plurality of teeth on the second opposing wall are arranged in parallel.

3. The system of claim 1, wherein a distance between the tips of teeth on the first and second opposing walls is about the diameter of an oocyte to be denuded.

4. The system of claim 1, wherein the plurality of teeth are set at an angle from about 39 degrees to less than 90 degrees against a direction of flow through the channel.

5. The system of claim 1, wherein at least one expansion unit has a width of about 250 to about 600 microns.

6. The system of claim 1, wherein at least one constriction unit has a width of about 100 to about 350 microns.

7. The system of claim 1,
wherein the channel comprises the inlet, the outlet, and at least three of the one or more stages arranged in series with each stage in fluid communication with the next stage,
wherein the first stage comprises a series of first expansion units alternating with first constriction units, wherein the first expansion units have a first width and the first constriction units have a second width, and a smooth internal surface;
wherein the second stage comprises a series of second expansion units alternating with second constriction units, wherein the second expansion units have a third width and the second constriction units have a fourth width, and a smooth internal surface; and
wherein the third stage comprises a series of third expansion units alternating with third constriction units, wherein the third expansion units have a fifth width and the third constriction units have a sixth width and at least two opposing walls,
wherein the two opposing walls each comprises a jagged internal surface comprising a plurality of teeth arranged in a manner that the plurality of teeth on a first opposing wall of the third constriction units are pointed towards the plurality of teeth on a second opposing wall of the third constriction units and wherein tips of the plurality of teeth on the first opposing wall and tips of the plurality of teeth on the second opposing wall are arranged in parallel.

8. The system of claim 7, wherein the first width is about 250 to about 600 microns, the second width is about 200 to about 350 microns, the third width is about 250 to about 600 microns, the fourth width is about 100 to about 250 microns, the fifth width is about 250 to about 600 microns, and wherein the sixth width is about 70 to about 120 microns.

9. The system of claim 7, wherein a distance between tips of the teeth on the first opposing wall and tips of the teeth on the second opposing wall is about 80 to 110 microns.

10. A method of removing cumulus cells from oocytes in a liquid sample, the method comprising:
obtaining a liquid sample comprising one or more oocytes;
injecting the liquid sample into the inlet of the system of claim 1;
flowing the liquid sample through the one or more stages of the channel at a flow rate; and
retrieving oocytes from the outlet.

11. The method of claim 10, wherein the liquid sample comprises follicular fluid, culture medium, or a buffer medium.

12. The method of claim 10, wherein the flow rate is approximately constant and is about 0.5 to about 5.0 ml/minute.

13. The method of claim 10, wherein the oocytes are human oocytes and a distance between tips of the plurality of teeth on the two opposing walls is about 100 to 110 microns.

14. A system for denuding oocytes from attached cumulus cells in a liquid sample, comprising:
a substrate; and
a channel comprising an inlet, an outlet, and one or more stages arranged in series between the inlet and the outlet,
wherein each stage is in fluid communication with a subsequent stage,
wherein each stage comprises one or more rows of a plurality of posts arranged across the channel, wherein posts in a given row are spaced apart from neighboring posts within the row to define a sub-channel between each neighboring pair of posts, and
wherein each of a plurality of posts in at least one stage includes a pair of walls arranged to face either an opposing wall of a neighboring post within a same row or to face an inner wall of the channel, and wherein at least one of the walls on each of the plurality of posts comprises a jagged internal surface comprising a plurality of teeth, and wherein the plurality of teeth are tilted against a direction of flow through the channel at a tilting angle of about 30 degrees to less than 90 degrees, wherein the tilting angle is an angle between the direction of flow and a median line of the teeth in the plurality of teeth.

15. The system of claim 14, wherein opposing walls of neighboring posts in a row each comprises a plurality of teeth arranged to point towards each other.

16. The system of claim 14, wherein at least one sub-channel of a first stage comprises a width of about 240 to 260 microns, wherein at least one sub-channel of a second stage comprises a width of about 140 to 160 microns, and wherein the first or the second stage, or both stages, comprises rows of posts arranged to filter debris from the fluid sample.

17. The system of claim 16, wherein at least one sub-channel in a third stage comprises a width of about 90 to 110 microns, wherein the third stage comprises rows of posts arranged to denude oocytes, and wherein one or more posts in each row of the third stage comprises a plurality of jagged teeth.

* * * * *